United States Patent [19]

Sitzmann

[11] Patent Number: 5,194,103
[45] Date of Patent: Mar. 16, 1993

[54] HIGH DENSITY ENERGETIC MATERIALS

[75] Inventor: Michael E. Sitzmann, Adelphi, Md.

[73] Assignee: The United States of America as represented by the Secretary of the Navy, Washington, D.C.

[21] Appl. No.: 695,144

[22] Filed: Apr. 30, 1991

[51] Int. Cl.$^5$ .................... C06B 45/10; C07C 257/06
[52] U.S. Cl. ...................... 149/19.1; 149/88; 558/6; 558/8
[58] Field of Search ..................... 149/19.1, 88; 558/6, 558/8

[56] References Cited

U.S. PATENT DOCUMENTS

| | | | |
|---|---|---|---|
| 3,700,708 | 10/1972 | Petry | 149/119 |
| 3,922,311 | 11/1975 | Peters et al. | 149/88 |
| 4,120,710 | 10/1978 | Peters et al. | 149/88 |
| 4,813,186 | 5/1989 | Sitzmann et al. | 560/148 |
| 4,849,540 | 7/1989 | Sitzmann et al. | 149/88 |
| 5,025,102 | 6/1991 | Sitzmann | 558/6 |

*Primary Examiner*—Edward A. Miller
*Attorney, Agent, or Firm*—Kenneth E. Walden; Roger D. Johnson

[57] ABSTRACT

Energetic compounds of the formula $$SF_5N=C-R_1$$
$$\phantom{SF_5N=C-}|$$
$$\phantom{SF_5N=C}R_2$$

wherein $R_1$ is $-OCH_2CH_2C(NO_2)_3$, $-OCH_2C(NO_2)_2CH_3$, $-OCH_2C(NO_2)_3$, $-OCH_2CF(NO_2)_2$, $-OCH_2CF_2(NO_2)$, or $-OCH_2CF_3$, and wherein $R_2$ is $-OCH_2CH_2C(NO_2)_3$, $-OCH_2CF(NO_2)_2$, $-OCH_2CF_2(NO_2)$, $-OCH_2CF_3$, $-NH_2$, $-NHCH_2CH_2ONO_2$, or $-N(NO_2)CH_2CH_2ONO_2$.

18 Claims, No Drawings

HIGH DENSITY ENERGETIC MATERIALS

CROSS REFERENCE TO RELATED APPLICATIONS

This is a continuation-in-part of copending applictaion Ser. No. 07/553,835, filed on Jul. 18, 1990 and now abandoned.

BACKGROUND OF THE INVENTION

This invention relates to explosives and more particularly high energy organic explosives.

The synthesis of 2-fluoro-2,2-dinitroethylchloroformate, $(NO_2)_2FCCH_2OC(O)Cl$, for use as an intermediate in preparation of energetic compounds was reported by J. P. Senet and C. Ucciani in a French patent (Fr. Demande 2,337,228; May 6, 1977). A limitation of 2-fluoro-2,2-dinitroethylchloroformate is that energetic derivatives from this intermediate do not generally have unusually high densities or oxidant balances. For energetic materials, density is a critical property since the performance of the material is proportional to the square of its density. The oxidant balance of an energetic material is also an important property since energetic plasticizers and explosives with high oxidant balance are preferable for use in explosive formulations (essentially all explosive formulations are fuel rich and extra oxidant will produce additional energy).

Therefore it would be desirable to provide new explosives having higher densities and energies and also higher oxidant balances.

SUMMARY OF THE INVENTION

Accordingly, an object of this invention to provide new explosives.

Another object of this invention is to provide new high density, energetic explosives.

A further object of this invention is to provide new high energy explosives having high oxidant balances.

These and other objectives of this invention are accomplished by providing compounds of the formula

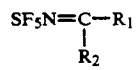

wherein $R_1$ is $-OCH_2CH_2C(NO_2)_3$, $-OCH_2C(NO_2)_2CH_3$, $-OCH_2C(NO_2)_3$, $-OCH_2CF(NO_2)_2$, $-OCH_2CF_3(NO_2)$, or $-OCH_2CF_3$, and wherein $R_2$ is $-OCH_2CH_2C(NO_2)_3$, $-OCH_2CF_2(NO_2)$, $-OCH_2CF_2(NO_2)$, $-OCH_2CF_3$, $-NH_2$, $-NHCH_2CH_2ONO_2$, or $-N(NO_2)CH_2CH_2ONO_2$, and wherein $R_1$ and $R_2$ may be the same or different.

DETAILED DESCRIPTION OF THE PREFERRED EMBODIMENT

Energetic compounds of the formula

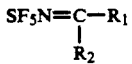

are prepared by reacting pentafluorosulfanyldichloroimine, $SF_5N=CCl_2$, with an alcohol $R_1H$ in a 1:1 molar ratio in the presence of a base, such as pyridine, to produce a compound of the formula

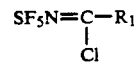

and then reacting the compound (II) with a compound of the formula $R_2H$ in a 1:1 molar ration, in the presence of a base (e.g., pyridine) when $R_2H$ is an alcohol, to produce the compound

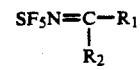

wherein $R_1$ is preferably $-OCH_2CH_2C(NO_2)_3$, $-OCH_2C(NO_2)_2CH_3$, $-OCH_2C(NO_2)_3$, $-OCH_2CF(NO_2)_2$, $-OCH_2CF_2(NO_2)$, or $-OCH_2CF_3$, and $R_2$ is preferably $-OCH_2CH_2C(NO_3)_3$, $-OCH_2CF(NO_2)_2$, $-OCH_2CF_2(NO_2)$, $-OCH_2CF_3$, $-NH_2$, $-NHCH_2CH_2ONO_2$, or $-N(NO_2)CH_2CH_2ONO_2$. Of these groups $-OCH_2C(NO_2)_3$ and $-OCH_2C(NO_2)_2CH_3$ are less preferred because care must be taken to avoid deformylation under basic reaction conditions. The groups $OCH_2CF_3$, and $-OCH_2CF_2(NO_2)$ are less preferred because of their low explosive content. Therefore $R_1$ is more preferably $-OCH_2CH_2C(NO_2)_3$ or $-OCH_2CF(NO_2)_2$. $R_1$ is most preferably $-OCH_2CF(NO_2)_2$ because this group combines superior stability with excellent explosive content. Similarly, $R_2$ is more preferably $-OCH_2CH_2C(NO_2)_3$, $-OCH_2CF(NO_2)_2$, $-NH_2$, $-NHCH_2CH_2ONO_2$, or $-N(NO_2)CH_2CH_2ONO_2$. $R_2$ is still more preferably $-CH_2CH_2C(NO_2)_3$, $-NH_2$, $-NHCH_2CH_2ONO_2$, or $N(NO_2)CH_2CH_2ONO_2$.

All of the compounds in this invention are useful as energetic ingredients for explosives or propellants. However, some of the compounds will find use as high-melting solid ingredients whereas other will be useful as low melting energetic plasticizers. When $R_1=R_2$ the melting point generally will be higher than when $R_1 \neq R_2$. Likewise, $-NNO_2$ groups tend to raise the melting points of these compounds. For example,

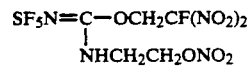

has a melting point of 4° C. (see Example 5) whereas

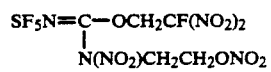

has a melting point of 76°–77° C. (see Example 6). Using mixtures of compounds will also depress the melting point.

A prior art method of preparing the starting material pentafluorosulfanyldichloroimine, $SF_5N=CCl_2$, is presented after the examples.

In the first step of the synthesis, each mole of pentafluorosulfanyldichloroimine is reacted with one mole of an energetic alcohol which is preferably 3,3,3-trinitropropanol, 2,2-dinitropropanol, 2,2,2-trinitroethanol, 2-fluoro-2,2-dinitroethanol, 2,2-difluoro-2-nitroethanol, 2,2,2-trifluoroethanol, or mixtures thereof. More preferred energetic alcohols are 3,3,3-trinitropropanol, 2-fluoro-2,2-dinitroethanol, or mixture thereof, with 2-fluoro-2,2-dinitroethanol being still more preferred.

The product of the reaction will preferably be 3,3,3-trinitropropylchloroformate, pentafluorosulfanylimine [SF$_5$N=C(Cl)OCH$_2$CH$_2$C(NO$_2$)$_3$]; 2,2-dinitropropylchloroformate, pentafluorosulfanylimine [SF$_5$N=C(Cl)OCH$_2$C(NO$_2$)$_2$CH$_3$]; 2,2,2-trinitroethylchloroformate, pentafluorosulfanylimine [SF$_5$N=C(Cl)OCH$_2$C(NO$_2$)$_3$]; 2-fluoro-2,2-dinitroethylchloroformate, pentafluorosulfanylimine [SF$_5$N=C(Cl)OCH$_2$CF(NO$_2$)$_2$]; 2,2-difluoro-2-nitroethylchloroformate, pentafluorosulfanylimine [SF$_5$N=C(Cl)OCH$_2$CF$_2$(NO$_2$)]; 2,2,2-trifluoroethylchloroformate, pentafluorosulfanylimine [SF$_5$N=C(Cl)OCH$_2$CF$_3$]; or mixtures thereof. More preferably the product will be 3,3,3-trinitropropylchloroformate, pentafluorosulfanylimine; 2-fluoro-2,2-dinitroethylchloroformate, pentafluorosulfanylimine; or mixtures thereof. Most preferably the product will be 2-fluoro-2,2-dinitroethylchloroformate, pentafluorosulfanylimine. This first reaction is run at low temperature preferably from about 0° C. to about 10° C., and more preferably from 0° C. to 5° C. This reaction is run in the presence of a base such as pyridine, with pyridine being most preferred. The reaction is run in a suitable inert solvent such as a halohydrocarbon, preferably chloroform, dichloromethane, 1,1-dichloroethane, 1,2-dichloroethane, 1,1,1-trichloroethane, 1,1,2-trichloroethane, or mixture thereof, with dichloromethane being most preferred. Example 1 illustrates the preferred conditions for this first reaction step.

In the second reaction step, the pentafluorosulfanylchloroimine compound produced in the first reaction step is reacted with a compound which is 3,3,3-trinitropropanol, HOCH$_2$CH$_2$C(NO$_2$)$_3$; 2-fluoro-2,2-dinitroethanol, HOCH$_2$CF(NO$_2$)$_2$; 2,2-fluoro-2-nitroethanol, HOCH$_2$CF$_2$(NO$_2$); 2,2,2-trifluoroethanol, HOCH$_2$CF$_3$; ammonia, NH$_3$; ethanolamine, HOCH$_2$CH$_2$NH$_2$; or mixtures thereof. When ammonia or ethanolamine is reacted with the pentafluorosulfanylchloroimine compound no additional base is needed (see Example 3 and 4). However, for the remaining compounds the reaction is run in the presence of a base such as pyridine (see Example 2). For all of the compounds the reaction is preferably run at a temperature of from about 0° C. to 10° C. or more preferably from 0° C. to 5° C. The reaction is preferably run in a suitable inert solvent such as a halohydrocarbon, preferably chloroform, dichloromethane, 1,1-dichloroethane, 1,2-dichloroethane, 1,1,1-trichloroethane, 1,1,2-trichloroethane, or mixtures thereof, and most preferable dichloromethane.

Note that when ethanolamine is used in this second reaction step, a 2-hydroxyethyl containing carbamate is produced

To increase the energy of this compound the —NHCH$_2$CH$_2$OH group is nitrated to form a —NHCH$_2$CH$_2$ONO$_2$ group. Conditions for this nitration are illustrated by example 5. An even more energetic compound is formed by nitrating the —NHCH$_2$CH$_2$ONO$_2$ group under more sever conditions to produce a —N(NO$_2$)CH$_2$CH$_2$ONO$_2$ group. Suitable conditions for this nitration are illustrated by example 6.

Compounds produced by the process include

SF$_5$N=C[OCH$_2$CH$_2$C(NO$_2$)$_3$]$_2$,
SF$_5$N=C[OCH$_2$CH$_2$C(NO$_2$)$_3$][OCH$_2$C(NO$_2$)$_2$CH$_3$],
SF$_5$N=C[OCH$_2$CH$_2$C(NO$_2$)$_3$][OCH$_2$CF(NO$_2$)$_2$],
SF$_5$N=C[OCH$_2$CH$_2$C(NO$_2$)$_3$][OCH$_2$CF$_2$(NO$_2$)],
SF$_5$N=C[OCH$_2$CH$_2$C(NO$_2$)$_3$](OCH$_2$CF$_3$),
SF$_5$N=C[OCH$_2$CH$_2$C(NO$_2$)$_3$](NH$_2$),
SF$_5$N=C[OCH$_2$CH$_2$C(NO$_2$)$_3$](NHCH$_2$CH$_2$ONO$_2$),
SF$_5$N=C[OCH$_2$CH$_2$C(NO$_2$)$_3$][N(NO$_2$)CH$_2$CH$_2$ONO$_2$],
SF$_5$N=C[OCH$_2$C(NO$_2$)$_2$CH$_3$][OCH$_2$CF(NO$_2$)$_2$],
SF$_5$N=C[OCH$_2$C(NO$_2$)$_2$CH$_3$][OCH$_2$CF$_2$(NO$_2$)],
SF$_5$N=C[OCH$_2$C(NO$_2$)$_2$CH$_3$](OCH$_2$CF$_3$),
SF$_5$N=C[OCH$_2$C(NO$_2$)$_2$CH$_3$](NH$_2$),
SF$_5$N=C[OCH$_2$C(NO$_2$)$_2$CH$_3$](NHCH$_2$CH$_2$ONO$_2$),
SF$_5$N=C[OCH$_2$C(NO$_2$)$_2$CH$_3$][N(NO$_2$)CH$_2$CH$_2$ONO$_2$],
SF$_5$N=C[OCH$_2$C(NO$_2$)$_3$][OCH$_2$CH$_2$C(NO$_2$)$_3$],
SF$_5$N=C[OCH$_2$C(NO$_2$)$_3$][OCH$_2$CF(NO$_2$)$_2$],
SF$_5$N=C[OCH$_2$C(NO$_2$)$_3$][OCH$_2$CF$_2$(NO$_2$)],
SF$_5$N=C[OCH$_2$C(NO$_2$)$_3$](OCH$_2$CF$_3$),
SF$_5$N=C[OCH$_2$C(NO$_2$)$_3$](NH$_2$),
SF$_5$N=C[OCH$_2$C(NO$_2$)$_3$](NHCH$_2$CH$_2$ONO$_2$),
SF$_5$N=C[OCH$_2$C(NO$_2$)$_3$][N(NO$_2$)CH$_2$CH$_2$ONO$_2$];
SF$_5$N=C[OCH$_2$CF(NO$_2$)$_2$]$_2$,
SF$_5$N=C[OCH$_2$CF(NO$_2$)$_2$][OCH$_2$CF$_2$(NO$_2$)],
SF$_5$N=C[OCH$_2$CF(NO$_2$)$_2$](OCH$_2$CF$_3$),
SF$_5$N=C[OCH$_2$CF(NO$_2$)$_2$](NH$_2$),
SF$_5$N=C[OCH$_2$CF(NO$_2$)$_2$](NHCH$_2$CH$_2$ONO$_2$),
SF$_5$N=C[OCH$_2$CF(NO$_2$)$_2$][N(NO$_2$)CH$_2$CH$_2$ONO$_2$],
SF$_5$N=C[OCH$_2$CF$_2$(NO$_2$)]$_2$,
SF$_5$N=C[OCH$_2$CF$_2$(NO$_2$)](OCH$_2$CF$_3$),
SF$_5$N=C[OCH$_2$CF$_2$(NO$_2$)](NH$_2$),
SF$_5$N=C[OCH$_2$CF$_2$(NO$_2$)](NHCH$_2$CH$_2$ONO$_2$),
SF$_5$N=C[OCH$_2$CF$_2$(NO$_2$)][N(NO$_2$)CH$_2$CH$_2$ONO$_2$],
SF$_5$N=C(OCH$_2$CF$_3$)$_2$,
SF$_5$N=C(OCH$_2$CF$_3$)(NH$_2$),
SF$_5$N=C(OCH$_2$CF$_3$)(NHCH$_2$CH$_2$ONO$_2$),
SF$_5$N=C(OCH$_2$CF$_3$)[N(NO$_2$)CH$_2$CH$_2$ONO$_2$].

The pentafluorosulfanylimine chloroformates, carbonates, and carbamates of this invention differ from conventional chloroformates, carbonates, and carbamates in that they contain a pentafluorosulfanylimine group,

rather than a carbonyl group,

As illustrated by Table 1, the pentafluorofanylimine group provides energetic compounds having greater densities and higher oxidant balances than the corresponding carbonyl compounds. The greater the density, the more energetic the explosive. Higher oxidant balances mean that less oxidizer material is required.

TABLE 1

| [(NO$_2$)$_2$FCCH$_2$O](R)C = X | | | | |
|---|---|---|---|---|
| | Density (g/cc) | | Oxidant Balance, OB$_{100}$ | |
| R | X = NSF$_5$ | X = O | X = NSF$_5$ | X = O |
| OCH$_2$CH$_2$C(NO$_2$)$_3$ | 1.74[a] | 1.59[a] | 2.80 | 1.87 |
| NH$_2$ | 1.81[b] | 1.60[a] | 2.48 | 0.01 |
| | 1.85[a] | | | |

TABLE 1-continued

| | [(NO$_2$)$_2$FCCH$_2$O](R)C = X | | | |
|---|---|---|---|---|
| | Density (g/cc) | | Oxidant Balance, OB$_{100}$ | |
| R | X = NSF$_5$ | X = O | X = NSF$_5$ | X = O |
| NH(CH$_2$)$_2$ONO$_2$ | 1.75$^c$ 1.74$^a$ | 1.53$^a$ | 1.70 | 0.00 |
| NNO$_2$(CH$_2$)$_2$ONO$_2$ | 1.98$^d$ | 1.79$^a$ | 2.63 | 1.51 |

$^a$calculated density.
$^b$experimental liquid density at 30° C.
$^c$experimental liquid density at 25° C.
$^d$experimental crystal density (x-ray).

The calculated densities in Table 1 were calculated according to a method taught by Cichra, D. A., Holden, J. R. and Dickinson, C., "Estimation of Normal Densities of Explosive Compounds from Empirical Atomic Volumes," NSWC TR 79–273, February, 1980, Naval Surface Weapons Center, Silver Spring, Md.

The oxidant balance (OB$_{100}$) was calculated by the method taught by M. J. Kamlet and H. G. Adolph, Proceedings of Seventh Symposium (International) on Detonation, June 16–19, 1981, Annapolis, Md., page 85. Oxidant balance (OB$_{100}$) is defined as the number of equivalents of oxidant per 100 grams of explosive above the amount required to burn all hydrogen to H$_2$O and HF and all carbon to CO and is represented by the equation, $$OB_{100} = \frac{100(2n_O + n_F - n_H - 2n_C - 2n_{COO})}{\text{molecular weight}}$$

where $n_O$, $n_F$, $n_H$, and $n_C$ represent the number of atoms of the respective elements in the molecule, and $n_{COO}$ is the number of carboxy groups. Sulfur is considered equivalent to oxygen since S gives the equivalent oxidation products of COS and H$_2$S.

Conventional plastic bonded explosives may be improved by incorporating an energetic plasticizer which is SF$_5$N=C[OCH$_2$CH$_2$C(NO$_2$)$_3$][OCH$_2$CF(NO$_2$)$_2$], SF$_5$N=C[NH$_2$][OCH$_2$CF(NO$_2$)$_2$], SF$_5$N=C[NHCH$_2$CH$_2$ONO$_2$][OCH$_2$CF(NO$_2$)$_2$], or mixtures thereof. SF$_5$N=C[OCH$_2$CH$_2$C(NO$_2$)$_3$][OCH$_2$CF(NO$_2$)$_2$] and SF$_5$N=C[NHCH$_2$CH$_2$ONO$_2$][OCH$_2$CF(NO$_2$)$_2$] are preferred as plasticizers because they are liquids at room temperature. SF$_5$N=C[OCH$_2$CH$_2$C(NO$_2$)$_3$][OCH$_2$CF(NO$_2$)$_2$] is the most preferred plasticizer because of its low melting point, high energy content, and high stability.

The general nature of the invention having been set forth, the following examples are presented as specific illustrations thereof. It will be understood that the invention is not limited to these specific examples, but is susceptible to various modifications that will be recognized by one of ordinary skilled in the art.

EXAMPLE 1

2-Fluoro-2,2-dinitroethylchloroformate, pentafluorosulfanylimine

A solution of 2.85 g (0.013 mole) of pentafluorosulfanyldichloroimine and 2.2 g (0.014 mole) of 2-fluoro-2,2-dinitroethanol in 10 ml of dichloromethane was stirred in an ice bath during the dropwise addition of 1.0 g (0.0125 mole) of pyridine in 8 ml of dichloromethane over 15 minutes. The reaction solution was stirred at 0° C. for 40 minutes before dilute hydrochloric acid was added after which the dichloromethane solution was separated and dried over sodium sulfate. The volatiles were removed to give 4.2 g of liquid which was chromatographed on Silica gel 40 using dichloromethane-hexanes (50/50) as eluent to give 3.6 g (84%) of pure 2-fluro-2,2-dinitroethylchloroformate, pentafluorosulfanylimine as a liquid; $^1$H-NMR (CDCl$_3$): 5.46 (d); IR (film): 1665 (C=N), 1610 (NO$_2$), 880–790 (SF$_5$) cm$^{-1}$. Anal Calcd. for C$_3$H$_2$ClF$_6$N$_3$O$_5$S: C, 10.55; H, 0.59; F, 33.37; N, 12.30; S, 9.39. Found: C, 10.58; H, 0.64; F, 33.27; N, 12.41; S, 10.05.

EXAMPLE 2

(2-Fluoro-2,2-dinitroethyl)(3,3,3-trinitropropyl)carbonate, pentafluorosulfanylimine To a solution of 0.7 g (0.002 mole) of 2-fluoro-2,2-dinitroethylchloroformate, pentafluorosulfanylimine and 0.65 g (0.0033 mole) 3,3,3-trinitropropanol in 7 ml of dichloromethane stirred at 0° C. was added 0.17 g (0.0022 mole) of pyridine in 2 ml of dichloromethane. The reaction solution was stored in a refrigerator at approximately 3° C. for 44 hours before dilute hydrochloric acid was added. The dichloromethane solution was separated and dried over sodium sulfate before the volatiles were removed to give 1.2 g of oil. Chromatography on Silica gel 40 using dichloromethane-hexanes (50/50) as eluent gave 0.6 g (60%) of pure (2-fluoro-2,2-dinitroethyl)(3,3,3-trinitropropyl) carbonate, pentafluorosulfanylimine which was stirred under very cold hexanes to give solid (2-fluoro-2,2-dinitroethyl)(3,3,3-trinitropropyl) carbonate, pentafluorosulfanylimine (mp 2° C.); $^1$H-NMR (CDCl$_3$): 3.66 (t, 2 H); 4.83 (t, 2 H); 5.38 (d, 2 H); IR (film): 1680 (C=N); 1610 (NO$_2$); 870–790 (SF$_5$)cm$^{-1}$. Anal Calculated for C$_6$H$_6$F$_6$N$_6$O$_{12}$S: C, 14.41; H, 1.21; F, 22.79; N. 16.80; S, 6.41. Found: C, 14.33; H, 1.27; F, 22.87; N, 16.72; S, 6.63.

EXAMPLE 3

2-Fluoro-2,2-dinitroethyl carbamate, pentafluorosulfanylimine

A solution of 2.0 g (0.0058 mole) of 2-fluoro-2,2-dinitroethylchloroformate, pentafluorosulfanylimine in 8 ml of dichloromethane stirred at 0° C. was carefully exposed to ammonia gas for approximately 3 hours until thin-layer chromatographic (TLC) analysis indicated that no 2-fluoro-2,2-dinitroethylchloroformate, pentafluorosulfanylimine remained. The reaction mixture was extracted with 2×20 ml of water before the dichloromethane solution was dried over sodium sulfate and the volatiles were removed to give 1.90 g of oil. Chromatography on Silica gel 60 gave 1.84 g (98%) of 2-fluoro- 2,2-dinitroethyl carbamate, pentafluorosulfanylimine mp 28.5°–30° C.; $^1$H-NMR (CDCl$_3$): 5.33 (d); 5.58 (broad, NH$_2$); IR (film): 3670, 3455 (NH$_2$), 1690 (C=N); 1610 (NO$_2$), 900–800 (SF$_5$)cm$^{-1}$. Anal. Calculated for C$_3$H$_4$F$_6$N$_4$O$_5$S: C, 11.18; H, 1.25; F, 35.39; N, 17.39; S, 9.95. Found: C, 11.06; H, 1.18; F, 35.71; N, 17.57; S, 9.77.

The liquid density of 2-fluoro-2,2-dinitroethyl carbamate, pentafluorosulfanylimine at 30° C. was measured via a pycnometer and found to be 1.81 g/cc.

EXAMPLE 4

N-(2-hydroxyethyl)-2-fluoro-2,2-dinitroethyl carbamate, pentafluorosulfanylimine To a solution of 0.7 g (0.002 mole) of 2-fluoro-2,2-dinitrochloroformate, pentafluorosulfanylimine in 5 ml of dichloromethane stirred at 0° C. was added 0.25 g (0.004 mole) of ethanolamine in 5 ml of dichloromethane dropwise over 10 minutes. After 1.5 hours at 0° C., dilute hydrochloric acid was added. The dichloromethane solution was separated, dried over sodium sulfate and the volatiles were removed to give 0.8 g (100%) of N-(2-hydroxyethyl)-2-fluoro-2,2-dinitroethyl carbamate, pentafluorosulfanylimine as an oil; $^1$H-NMR (CDCl$_3$+D$_2$O): 3.45 (t, 2 H); 3.85 (t, 2 H); 5.36 (d, 2 H); 6.15 (broad, NH); IR (film): 3725–3200 (NH, OH), 1670 (C=N), 1610 (NO$_2$), 900–870 (SF$_5$)cm$^{-1}$.

EXAMPLE 5

N-(2-nitroxyethyl)-2-fluoro-2,2-dinitroethyl carbamate, pentafluorosulfanylimine A solution of 0.65 g (0.0018 mole) of N-(2-hydroxyethyl)-2-fluoro-2,2-dinitroethyl carbamate, pentafluorosulfanylimine in 20 ml of dichloromethane was stirred vigorously at 0° C. as 2 ml of 90% nitric acid was added dropwise. After 1 hour 45 minutes at 0° C., ice water was added and the dichloromethane solution was separated and dried over sodium sulfate. Removal of the volatiles gave 0.73 g (100%) of an oil which was chromatographed on Silica gel 40 (dichloromethane-hexanes, 50/50, as eluent) to give 0.59 g (81%) of pure N-(2-nitroxyethyl)-2-fluoro-2,2-dinitroethyl carbamate, pentafluorosulfanylimine as an oil. Stirring the oil in very cold hexanes containing a very small amount of dichloromethane gave crystals, mp 4° C.; $^1$H-NMR (CDCl$_3$): 3.68 (m, $_2$ H), 4.65 (t, 2 H), 5.38 (d, 2 H), 5.97 (broad, NH); IR (film): 3490 (NH), 1675 ((C=N), 1650 (ONO$_2$), 1615 (NO$_2$), 900–790 (SF$_5$)cm$^{-1}$. Anal. Calculated for C$_5$H$_7$F$_6$N$_5$O$_8$S: C, 14.60; H, 1.72; F, 27.72; N, 17.03; S, 7.80. Found: C, 14.67; H, 1.82; F, 27.41; N, 17.33; S, 7.84.

The liquid density of N-(2-nitroxyethyl)-2-fluoro-2,2-dinitroethyl carbamate, pentafluorosulfanylimine was determined via pycnometer to be 1.75 g/cc.

EXAMPLE 6

N-Nitro-N-(2-nitroxyethyl)-2-fluoro-2,2-dinitroethyl carbamate, pentafluorosulfanylimine To 6 ml of trifluoroacetic anhydride stirred in an ice bath was added 0.6 ml of 100% nitric acid dropwise. Then 0.40 g (0.001 mole) of N-(2-nitroxyethyl)-2-fluoro-2,2-dinitroethyl carbamate, pentafluorosulfanylimine was added and, after 1 hour at 0° C., a solid had precipitated from solution. The reaction mixture was poured onto ice to give a solid, mp 75°–77° C. Crystallization from chloroform gave crystals of N-nitro-N-(2-nitroxyethyl)-2-fluoro-2,2-dinitroethyl carbamate, pentafluorosulfanylimine, mp 76°–77° C.; $^1$H-NMR (CDCl$_3$): 4.27 (t, 2 H); 4.85 (t, 2 H); 5.49 (d, 2 H); IR (KBr): 1700 (C=N), 1655 (ONO$_2$), 1615 (NO$_2$), 1585 (N-NO$_2$); 900–800 (SF$_5$)cm$^{-1}$.

The crystal structure of N-nitro-N-(2-nitroxyethyl)-2-fluoro-2,2-dinitroethyl carbamate, pentafluorosulfanylimine was determined (x-ray) and its crystal density was found to be 1.98 g/cc.

EXAMPLE 7

3,3,3-Trinitropropylchloroformate, pentafluorosulfanylimine

A solution of 0.9 g (0.004 mole) of pentafluorosulfanyldichloroimine and 0.95 g (0.0048 mole) of 3,3,3-trinitropropanol in 8 ml of dichloromethane was stirred in an ice bath during the dropwise addition of 0.35 g (0.0044 mole) of pyridine in 3.5 ml of dichloromethane. After 1 hour at 0° C., cold dilute hydrochloric acid was added and the dichloromethane solution was separated and dried over sodium sulfate. Removal of volatiles gave 1.70 g of oil which was chromatographed on Silica gel 40 using dichloromethane-hexanes (60/40) as eluent to give 1.18 g (77%) of 3,3,3-trinitropropylchloroformate, pentafluorosulfanylimine as an oil. H-NMR (CDCl$_3$): 3.63 (t, 2 H), 4.83 (t, 2 H). IR (film): 1660 (C=N), 1610 (NO$_2$), 920–770 (SF$_5$).

EXAMPLE 8

3,3,3-Trinitropropyl carbamate, pentafluorosulfanylimine

A solution of 0.66 9 (0.0017 mole) of 3,3,3-trinitropropylchloroformate, pentafluorosulfanylimine in 15 ml of dichloromethane was stirred in an ice bath while ammonia gas was slowly added until thin-layer chromatography (TLC) analysis showed no starting material remained. The mixture was filtered and the volatiles were removed from the filtrate to give 0.6 g of product. Chromatography on Silica gel 40 using dichloromethane-hexanes (70/30) as eluent gave 0.55 g (89%) of 3,3,3-trinitropropyl carbamate, pentafluorosulfanylimine (mp 43°–45° C.); $^1$H-NMR (CDCl$_3$): 3.57 (t, 2 H), 4.70 (t, 2 H), 5.42 (broad, 2 H). IR (KBR): 3560, 3440 (NH), 1680 (C=N), 1610 (NO$_2$), 890–790 (SF$_5$). Anal. Calculated for C$_4$H$_6$N$_5$F$_5$O$_7$S: C, 13.23; H, 1.66; N, 19.28; F, 26.16; S, 8.83. Found: C, 12.92; H, 1.59; N, 18.81; F, 26.55; S, 8.91.

EXAMPLE 9

Bis(3,3,3-trinitropropyl)carbonate, pentafluorosulfanylimine

Pyridine (0.9 g, 0.0114 mole) in 5 ml of dichloromethane was added slowly to a solution of 0.8 g (0.00357 mole) of pentafluorosulfanyldichloroimine and 3.3 g (0.0169 mole) of 3,3,3-trinitropropanol in 10 ml of dichloromethane stirred in an ice bath. The mixture was stored in a refrigerator at 3° C. for 48 hours before dilute hydrochloric acid was added and the dichloromethane solution was separated and dried over sodium sulfate. The volatiles were removed to give 3.7 g of oil which was chromatographed on Silica gel 40 (dichloromethane as eluent) to yield 0.8 g (42%) of essentially pure bis(3,3,3-trinitropropyl)carbonate, pentafluorosulfanylimine. Crystallization from chloroform-hexanes gave white crystals, mp 60°–61° C.; $^1$H-NMR(CDCl$_3$): 3.65 (t, 2 H), 4.77 (t, 2 H); IR(KBr): 1662 (C=N), 1610 (NO$_2$), 880–770 (SF$_5$). Anal. Calculated for C$_7$H$_8$N$_7$F$_5$SO$_{14}$: C, 15.53; H, 1.49; N, 18.12; F, 17.55; S, 5.92. Found: C, 15.58; H, 1.46; N, 17.70; F, 17.19; S, 5.90.

Preparation of Pentafluorosulfanyldichloroimine

Starting Material

A method of preparing the pentafluorosulfanyldichloroimine, SF$_5$N=CCl$_2$, starting material is taught by C. W. Tullock. et al., "Synthesis and Chemistry of SF$_5$Cl," *Journal of the American Chemical Society*, Vol. 86 (1964), pp. 357–61, at page 359, herein incorporated by reference in its entirety.

Tullock et al. first teach the synthesis of SF$_5$Cl:

Synthesis of Sulfur Chloride pentafluoride. Finally divided cesium fluoride (172 g., 1.13 moles), sulfur tetrafluoride (108 g., 1.00 mole), and chloride (71 g., 1.00 mole) were heated with agitation for 1 hr. at 100°, for 1 hr. at 150°, and for 2 hr. at 175° in a 500-ml. Hastelloy C steel pressure vessel. The volatile product recovered (100 g) was distilled through a low temperature still (still head cooled to $-60°$ since $SF_5Cl$ freezes at $-64°$). The colorless fraction distilling at $-23°$ to $-21°$ (lit. [4] reports $-21°$) amounted to 125 g.; . . . indicated the distillate contained at least 95% $SF_5Cl$.

The conversation was about 75% . . . Tullock et al. then teach the synthesis of $SF_5N=CCl_2$.

Addition of $SF_5Cl$ to CN-Containing Compounds. -All of the ultraviolet-light catalyzed reactions were carried out in a similar manner. The reactor, either a 12- or 22-l. Pyrex flask was provided with a quartz well, 1.5 in. in diameter and 16 in. deep, which extended from the neck into the center of the flask. A low-pressure mercury vapor resonance lamp, in the form of a tightly wound 10-in quartz spiral, 6 mm. in diameter, which was inserted into the well, was the ultraviolet light source. The lamp was powder by a 5000 v., 60-milliamp transformer. The reactor flask was evacuated behind a protective shield and the gaseous reactants were added in sufficient quantities so that their initial pressure ranged from 600 to 730 mm. pressure. Since the products were liquids, the extent of the reaction could be estimated by the decrease in pressure as reaction proceeded. When reaction stopped or slowed considerably, the reactants were removed and were purified by distillation either through a packed, low-temperature column or a spinning-band column.

A. Preparation of $SF_5N=CCl_2$. A 12-l., round-bottomed flask containing cyanogen chloride (14 g., 0.23 mole) and $SF_5Cl$ (37 g., 0.23 mole) was irradiated for 6.5 hr., after which the contents were transformed to a liquid nitrogen cooled, evacuated trap and then allowed to warm up gradually to room temperature. The liquid from two such experiments were combined to give 37 g., amounting to a 36% conversion, of colorless $SF_5=CCl_2$, b.p. $86°-88°$ . . .

Obviously, numerous modifications and variations of the present invention are possible in light of the foregoing teachings. It is therefore to be understood that within the scope of the appended claims the invention may be practiced otherwise than as specifically described.

What is claimed is:

1. A compound of the formula $SF_5N=C(Cl)R$ wherein R is $-OCH_2CH_2C(NO_2)_3$, $-OCH_2C(NO_2)_2CH_3$, $-OCH_2C(NO_2)_3$, $-OCH_2CF(NO_2)_2$, $-OCH_2CF_2(NO_2)$, or $-OCH_2CF_3$.

2. The compound of claim 1 wherein R is $-OCH_2CH_2C(NO_2)_3$ or $-OCH_2CF(NO_2)_2$.

3. The compound of claim 2 wherein R is $-OCH_2CF(NO_2)_2$.

4. A compound of the formula

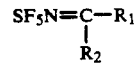

wherein $R_1$ is $-OCH_2CH_2C(NO_2)_3$, $-OCH_2C(NO_2)_2CH_3$, $-OCH_2C(NO_2)_3$, $-OCH_2CF(NO_2)_2$, $-OCH_2CF_2(NO_2)$, or $OCH_2CF_3$, and wherein $R_2$ is $-OCH_2CH_2C(NO_2)_3$, $CH_2CF(NO_2)_2$, $-OCH_2CF_2(NO_2)$, $OCH_2CF_3$, $-NH_2$, $-NHCH_2CH_2ONO_2$ or $-N(NO_2)CH_2CH_2ONO_2$, provided that if $R_1$ is $-OCH_2CF(NO_2)_2$ then $R_2$ is not $-OCH_2CF(NO_2)_2$.

5. The compound of claim 4 wherein $R_1$ is $-OCH_2CH_2C(NO_2)_3$ or $-OCH_2CF(NO_2)_2$.

6. The compound of claim 5 wherein $R_1$ is $-CH_2CF(NO_2)_2$.

7. The compound of claim 4 wherein $R_2$ is $-OCH_2CH_2C(NO_2)_3$, $-OCH_2CF(NO_2)_2$, $-NH_2$, $-NHCH_2CH_2ONO_2$, or $-N(NO_2)CH_2CH_2ONO_2$.

8. The compound of claim 7 wherein $R_2$ is $-OCH_2CH_2C(NO_2)_3$, $-NH_2$, $-NHCH_2CH_2ONO_2$, or $-N(NO_2)CH_2CH_2ONO_2$.

9. The compound of claim 4 wherein $R_1=R_2$.

10. The compound of claim 4 wherein $R_1 \neq R_2$.

11. A plastic bonded explosive wherein the improvement comprises using an energetic plasticizer of the formula

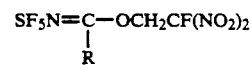

wherein R is $-OCH_2CH_2C(NO_2)_3$, $-NH_2$, $-NHCH_2CH_2ONO_2$, or mixtures thereof.

12. The plastic bonded explosive of claim 11 wherein the energetic plasticizer is

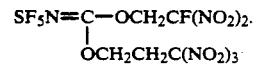

13. The plastic bonded explosive of claim 11 wherein the energetic plasticizer is

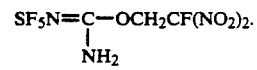

14. The plastic bonded explosive of claim 11 wherein the energetic plasticizer is

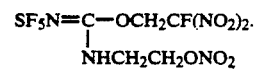

15. The compound of claim 4 that is $SF_5N=C[OCH_2CH_2C(NO_2)_3][OCH_2CF(NO_2)_2]$.

16. The compound of claim 4 that is $SF_5N=C[OCH_2CF(NO_2)_2](NH_2)$.

17. The compound of claim 4 that is $SF_5N=C[OCH_2CF(NO_2)_2](NHCH_2CH_2ONO_2)$.

18. The compound of claim 4 that is $SF_5N=C[OCH_2CH_2C(NO_2)_3](NH_2)$.

* * * * *